United States Patent
Pees et al.

(10) Patent No.: US 6,559,151 B2
(45) Date of Patent: May 6, 2003

(54) 6-(2-TRIFLUOROMETHYL-PHENYL)-TRIAZOLOPYRIMIDINES

(75) Inventors: Klaus Jüergen Pees, Mainz (DE); Frank Schieweck, Hessheim (DE); Jordi Tormo I Blasco, Limburgerhof (DE); Hubert Sauter, Mannheim (DE); Oliver Cullman, Heppenheim (DE); Bernd Müller, Frankenthal (DE); Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Eberhard Ammermann, Heppenheim (DE); Siegried Strathmann, Limburgerhof (DE); Gisela Lorenz, Hambach (DE); Rheinhard Stierl, Mutterstadt (DE)

(73) Assignee: BASF Aktiengesellschaft, Laudwigshafen (DE)

( * ) Notice: Subject to any disclaimer, the term of this patent is extended or adjusted under 35 U.S.C. 154(b) by 0 days.

(21) Appl. No.: 09/735,126

(22) Filed: Dec. 12, 2000

(65) Prior Publication Data
US 2002/0061882 A1 May 23, 2002

Related U.S. Application Data

(63) Continuation-in-part of application No. 09/566,339, filed on May 8, 2000, now abandoned.

(51) Int. Cl.⁷ .................. A01N 43/90; C07D 487/04
(52) U.S. Cl. .................. 514/259.31; 544/263
(58) Field of Search .................. 544/263; 514/259.31

(56) References Cited

U.S. PATENT DOCUMENTS

| | | | |
|---|---|---|---|
| 4,567,263 A | 1/1986 | Eicken et al. | 544/263 |
| 5,593,996 A * | 1/1997 | Pees | 514/258 |
| 5,612,345 A | 3/1997 | Becher et al. | 514/258 |
| 5,756,509 A | 5/1998 | Pees | 514/258 |
| 5,808,066 A | 9/1998 | Krummel et al. | 544/263 |
| 5,817,663 A | 10/1998 | Pees et al. | 544/263 |
| 5,965,561 A | 10/1999 | Pees et al. | 514/258 |
| 5,981,534 A | 11/1999 | Pfrengle | 514/258 |
| 6,117,865 A | 9/2000 | Pees | 514/212.01 |

FOREIGN PATENT DOCUMENTS

| | | | |
|---|---|---|---|
| EP | 0 071 792 A2 | 7/1982 | C07D/487/04 |
| EP | 0 550 113 B1 | 7/1993 | C07D/487/04 |
| EP | 0 613 900 | 9/1994 | C07D/487/04 |
| EP | 0 770 615 A1 | 5/1997 | C07D/487/04 |
| EP | 0 782 997 A | 7/1997 | C07D/487/04 |
| EP | 0 834 513 A | 4/1998 | C07D/487/04 |
| EP | 0 945 453 A | 9/1999 | C07D/487/04 |
| FR | 2795073 | 12/2000 | C07D/487/04 |
| WO | 0770615 | * 10/1996 | |
| WO | 98/46607 | 10/1998 | C07D/487/04 |
| WO | 98/46608 | 10/1998 | C07D/487/04 |
| WO | 99/48893 | 9/1999 | C07D/487/04 |

OTHER PUBLICATIONS

CAS printout for Becher et al.*

* cited by examiner

Primary Examiner—Richard L. Raymond
Assistant Examiner—Hong Liu
(74) Attorney, Agent, or Firm—Keil & Weinkauf

(57) ABSTRACT

6-(2-Trifluoromethyl-phenyl)-triazolopyrimidines of formula I

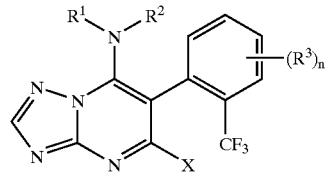

in which
R¹ and R² independently denote hydrogen or
alkyl, alkenyl, alkynyl, alkadienyl, or haloalkyl, cycloalkyl, bicycloalkyl, phenyl, naphthyl, or 5- or 6-membered heterocyclyl, containing one to four nitrogen atoms or one to three nitrogen atoms and one sulfur or oxygen atom, or
5- or 6-membered heteroaryl, containing one to four nitrogen atoms or one to three nitrogen atoms and one sulfur or oxygen atom, or
where R¹ and R² radicals may be unsubstituted or substituted as defined in the specification; or
R¹ and R² together with the interjacent nitrogen atom represents a 5- or 6-membered heterocyclic ring, containing one to four nitrogen atoms or one to three nitrogen atoms and one sulfur or oxygen atom, which may be substituted as defined in the specification;
R³ is hydrogen, halogen, alkyl, alkoxy and haloalkyl; and
X is halogen;
processes and intermediates for preparing these compounds, compositions comprising them and their use for controlling phytopathogenic fungi are described.

8 Claims, No Drawings

6-(2-TRIFLUOROMETHYL-PHENYL)-TRIAZOLOPYRIMIDINES

This application is a CIP of U.S. application Ser. No. 09/566,339, filed on May 8, 2000 now abandoned.

The invention relates to 6-(2-trifluoromethyl-phenyl)-triazolopyrimidines of formula I

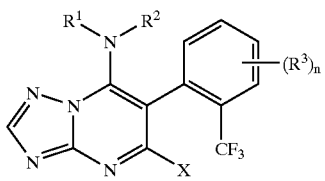

in which
R$^1$ and R$^2$ independently denote hydrogen or
  C$_1$–C$_{10}$-alkyl, C$_2$–C$_{10}$-alkenyl, C$_2$–C$_{10}$-alkynyl, C$_4$–C$_{10}$-alkadienyl, or C$_1$–C$_{10}$-haloalkyl,
  C$_3$–C$_8$-cycloalkyl, C$_5$–C$_{10}$-bicycloalkyl, phenyl, naphthyl, or 5- or 6-membered heterocyclyl, containing one to four nitrogen atoms or one to three nitrogen atoms and one sulfur or oxygen atom, or
  5- or 6-membered heteroaryl, containing one to four nitrogen atoms or one to three nitrogen atoms and one sulfur or oxygen atom, or
  where R$^1$ and R$^2$ radicals may be unsubstituted or partially or fully halogenated or may carry one to three groups R$^a$,
R$^a$ is halogen, cyano, nitro, hydroxyl, C$_1$–C$_6$-alkyl, C$_1$–C$_6$-haloalkyl, C$_3$–C$_6$-cycloalkyl, C$_1$–C$_6$-alkoxy, C$_1$–C$_6$-haloalkoxy, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_2$–C$_6$-alkynyl, C$_3$–C$_6$-alkynyloxy and C$_1$–C$_4$-alkylenedioxy, which may be halogenated; or
R$^1$ and R$^2$ together with the interjacent nitrogen atom represent a 5- or 6-membered heterocyclic ring, containing one to four nitrogen atoms or one to three nitrogen atoms and one sulfur or oxygen atom, which may be substituted by one to three R$^a$ radicals;
R$^3$ is hydrogen, halogen, C$_1$–C$_{10}$-alkyl, C$_1$–C$_{10}$-alkoaxy and C$_1$–C$_{10}$-haloalkyl;
n is 1, 2, or 3; and
X is halogen.

Moreover, the invention relates to processes for their preparation, compositions containing them and to their use for combating phytopathogenic fungi.

U.S. Pat. No. 4,567,263 discloses compounds of the formula

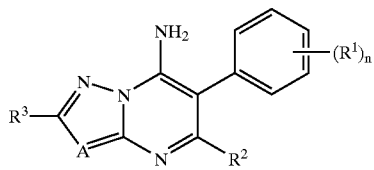

in which R$^1$ represents alkyl, halogen, alkoxy, cyano, cycloalkyl, aryl, aryloxy, arylthio, aralkyl, arylthio, arylalkyl, arylalkyloxy or arylalkylthio each optionally substituted by halogen or alkoxy; or (R$^1$)$_n$ represents a benzene, indane or tetrahydronaphthalene ring fused with the phenyl ring, aromatic moieties in the above groups being optionally substituted by alkyl, alkoxy, halogen or cyano; n is 1 or 2; R$^2$ and R$^3$ are each hydrogen, alkyl or aryl, A represents a nitrogen atom or a CR$^4$ group, and R$^4$ is as R$^2$ but can also be halogen, cyano or alkoxycarbonyl or together with R$^3$ can form an alkylene chain containing up to two double bonds. The compounds are said to be active against various phytopathogenic fungi.

U.S. Pat. No. 5,593,996 embraces compounds of the general formula

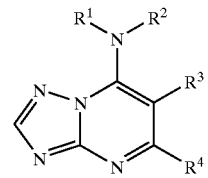

in which R$^1$ represents an optionally substituted alkyl, alkenyl, alkadienyl, cycloalkyl, bicycloalkyl or heterocyclyl group; R$^2$ represents a hydrogen atom or an alkyl group; or R$^1$ and R$^2$ together with the interjacent nitrogen atom represent an optionally substituted heterocyclic ring; R$^3$ represents an optionally substituted aryl group; and R$^4$ represents a hydrogen or halogen atom or a group -NR$^5$R$^6$ where R$^5$ represents a hydrogen atom or an amino, alkyl, cycloalkyl or bicycloalkyl group and R$^6$ represents a hydrogen atom or an alkyl group. These compounds are said to be active against fungi.

WO-A 98/46607 discloses funcidal triazolopyrimidines, which are substituted in the 6-position by a 2,4,6-trifluorophenyl group.

It is an object of the present invention to provide compounds having improved fungicidal activity.

We have found that this object is achieved by the compounds defined at the outset. Furthermore, we have found processes for their preparation, compositions comprising them and methods for controlling phytopathogenic fungi using the compounds I.

The compounds of the formula I differ from the compounds known from the abovementioned art in the 6-(2-trifluoromethyl)phenyl group.

The present invention further provides a process for the preparation of compounds of formula I as defined above which comprises treating a compound of formula IV

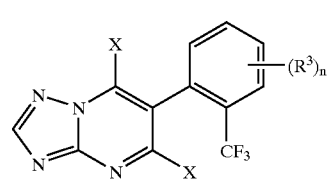

in which R$^3$, n and X are as defined in formula I; with an amine of formula V

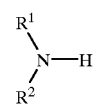

in which R$^1$ and R$^2$ are as defined in formula I to produce compounds of formula I.

Compounds of formula IV are novel and can be prepared by reacting 5-amino-triazole with 2-(2-trifluoromethyl-phenyl)-substituted malonic acid ester of formula II,

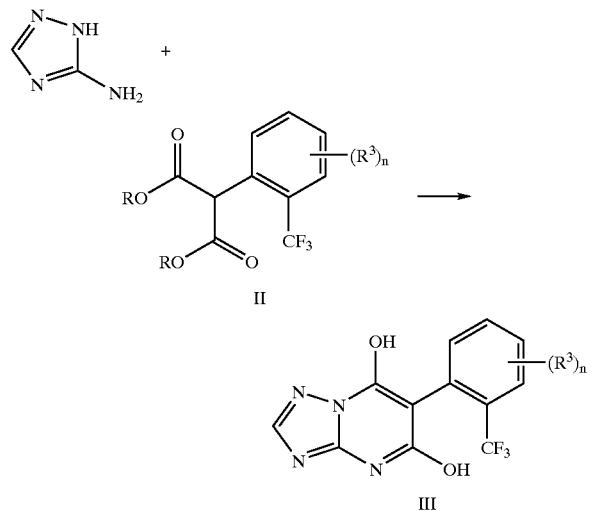

wherein $R^3$ and n are as defined for formula I, R represents alkyl, preferably $C_1$–$C_6$-alkyl, in particular methyl or ethyl, under alkaline conditions, preferably using high boiling tertiary amines as for example tri-n-butylamine as disclosed for example by EP-A770 615 to yield compounds of formula III.

The resulting 5,7-dihydroxy-6-phenyl-triazolopyrimidine of formula II;, wherein $R^3$ and n are as defined for formula I, is subsequently treated with a halogenating agent, preferably with a brominating or chlorinating agent, such as phosphorus oxybromide or phosphorus oxychloride, neat or in the presence of a solvent to give IV.

The reaction is suitably carried out at a temperature in the range from 0° C. to 150° C., the preferred reaction temperature being from 80° C. to 125° C. as disclosed for example by EP-A770 615.

The compounds of formula II are preferably prepared by reaction of the corresponding substituted bromobenzenes with sodium dialkylmalonates in the presence of a copper(I) salt [cf. Chemistry Letters, pp. 367–370, 1981].

The compounds of formula II are preferably prepared by reaction of an alkyl 2-(2-trifluoromethyl-phenyl)-acetate with dialkylcarbonate in the presence of a strong base, preferably sodium ethoxide and sodium hydride (cf. Heterocycles, pp. 1031–1047, 1996).

The reaction between the 5,7-dihalo-6-(2-fluoro-5-trifluorome-thyl-phenyl)-triazolopyrimidines of formula IV and the amine of formula V is preferably carried out in the presence of a solvent, Suitable solvents include ethers, such as dioxane, diethyl ether and, especially, tetrahydrofuran, halogenated hydrocarbons such as dichloromethane and aromatic hydrocarbons, for example toluene.

The reaction is suitably carried out at a temperature in the range from 0° C. to 70° C., the preferred reaction temperature being from 10° C. to 35° C.

It is also preferred that the reaction is carried out in the presence of a base. Suitable bases include tertiary amines, such as triethylamine, and inorganic bases, such as potassium carbonate or sodium carbonate. Alternatively, an excess of the compound of formula V may serve as a base.

Accordingly, the invention relates to the novel intermediates of formula IV, in particular 5,7-dichloro-6-(5-fluoro-2-trifluorome-thyl-phenyl)-[1,2,4]triazolo[1,5-α]pyrimidine, to the corresponding dialkyl-(3-fluoro-6-trifluoromethylphenyl)-malonates of formula II; and to 5,7-dihydroxy-6-(5-fluoro-2-trifluoromethyl-phenyl)-[1,2,4]triazolo[1,5-α]pyrimidine.

The substituted phenylacetates which are the starting compounds for compounds of formula II are known and commercially available, and/or they are obtainable by generally known methods.

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperatures. If the intermediates and end products are obtained as solids, purification can also be carried out by recrystallization or digestion.

If individual compounds I are not obtainable by the routes described above, they can be prepared by derivatization of other compounds I.

In the symbol definitions given in the formulae above, collective terms were used which generally represent the following substituents:

halogen: fluorine, chlorine, bromine and iodine;

$C_1$–$C_4$-alkyl and the alkyl moieties of $C_1$–$C_4$-alkoxy, $C_1$–$C_4$-alkylthio, $C_1$–$C_4$-alkylamino, di-$C_1$–$C_4$-alkylamine or $C_1$–$C_4$-alkylcarbonyloxy: saturated, straight-chain or branched hydrocarbon radicals having 1 to 4 carbon atoms, specifically methyl, ethyl, propyl, 1-methylethyl, butyl, 1-methylpropyl, 2-methylpropyl, 1,1-dimethylethyl;

$C_1$–$C_{10}$-alkyl and the alkyl moieties of $C_1$–$C_{10}$-haloalkyl: saturated, straight-chain or branched hydrocarbon radicals having 1 to 10, especially 1 to 6 carbon atoms, for example $C_1$–$C_4$-alkyl as mentioned above or pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_6$-alkoxy, $C_1$–$C_6$-alkylthio, $C_1$–$C_6$-alkylamino and di-$C_1$–$C_6$-alkylamine: saturated, straight-chain or branched hydrocarbon radicals having 1 to 6 carbon atoms, for example $C_1$–$C_4$-alkyl as mentioned above or pentyl, 1-methylbutyl, 2-methylbutyl, 3-methylbutyl, 2,2-di-methylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_4$-alkylene: methylene, ethylene, n-propylene or n-butylene;

$C_1$–$C_6$-haloalkyl and the haloalkyl moieties of $C_1$–$C_6$-haloalkoxy: straight-chain or branched alkyl groups having 1 to 6, preferably 1 to 4 carbon atoms (as mentioned above), where the hydrogen atoms in these groups may be partially or fully replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_2$–$C_{10}$-alkenyl: unsaturated, straight-chain or branched hydrocarbon radicals having 2 to 10, especially 2 to 6 carbon atoms and a double bond in any position, for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$–$C_{10}$-alkynyl: straight-chain or branched hydrocarbon radicals having 2 to 10, especially 2 to 4 carbon atoms and a triple bond in any position, for example ethynyl, 1-propynyl, 2-propynyl, 1-butynyl, 2-butynyl, 3-butynyl and 1-methyl-2-propynyl;

In general terms, the term cycloalkyl, as used herein with respect to a radical or moiety refers to a cycloalkyl group having 3 to 8 carbon atoms, preferably 5 to 7 carbon atoms.

In general terms, the term bicycloalkyl, as used herein with respect to a radical or moiety refers to a bicycloalkyl group having 5 to 10 carbon atoms, preferably 6 to 9 carbon atoms, in particular bicycloheptyl being optionally substituted by one or more halogen atoms, nitro, cyano, alkyl, preferably $C_1$–$C_6$ alkyl, alkoxy, preferably $C_1$–$C_6$ alkoxy.

Aryl: a mono- to tricyclic aromatic ring system containing 6 to 14 carbon ring members, for example phenyl, naphthyl and anthracenyl;

5-membered heteroaryl, containing one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

6-membered heteroaryl, containing one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

With respect to the phenyl radical, the term "with or without substitution" is intended to express that this radical may be partially or fully halogenated [i.e. the hydrogen atoms of this radical may be partly or wholly replaced by identical or different halogen atoms as mentioned above (preferably fluorine, chlorine or bromine, in particular fluorine or chlorine)] and/or carry one to four (in particular one to three) of the following radicals:

halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

With respect to their intended use, preference is given to triazolopyrimidines of the formula I having the following substituents, where the preference is valid in each case on its own or in combination:

The particularly preferred embodiments of the intermediates with respect to the variables correspond to those of the radicals X, $R^1$, $R^2$ and $R^3$ of formula I.

A preferred alkyl moiety is an ethyl or especially a methyl group.

A preferred haloalkyl moiety is the 2,2,2-trifluoroethyl or 1,1,1-trifluoroprop-2-yl group;

A preferred alkenyl moiety is allyl or especially a 2-methylallyl group.

A preferred cycloalkyl moiety is cyclopentyl being optionally substituted by one or more halogen atoms, nitro, cyano, alkyl, preferably $C_1$–$C_6$ alkyl, alkoxy, preferably $C_1$–$C_6$ alkoxy.

A preferred aryl moiety is phenyl being optionally substituted by one or more halogen atoms, nitro, cyano, alkyl, preferably $C_1$–$C_6$ alkyl, alkoxy, preferably $C_1$–$C_6$ alkoxy.

A preferred heteroaryl moiety is pyridyl, pyrimidyl, pyrazolyl or thienyl.

A preferred heterocyclyl moiety is pyrrolodinyl, pyrrazolidinyl, piperidinyl, piperazinyl or morpholin-4-yl being optionally substituted by one or more halogen atoms, nitro cyano, alkyl, preferably $C_1$–$C_6$ alkyl, alkoxy, preferably $C_1$–$C_6$ alkoxy.

X represents a fluorine, chlorine, bromine or iodine atom, in particular a chlorine atom.

Preference is given to compounds of formula I in which any alkyl or haloalkyl part of the groups $R^1$ or $R^2$, which may be straight chained or branched, contains up to 10 carbon atoms, preferably 1 to 9 carbon atoms, more preferably 2 to 6 carbon atoms, any alkenyl or alkynyl part of the substituents $R^1$ or $R^2$ contains up to 10 carbon atoms, preferably 2 to 9 carbon atoms, more preferably 3 to 6 carbon atoms, any cycloalkyl part of the substituents $R^1$ or $R^2$ contains from 3 to 10 carbon atoms, preferably from 3 to 8 carbon atoms, more preferably from 3 to 6 carbon atoms, any bicycloalkyl part of the substituents $R^1$ or $R^2$ contains from 5 to 9 carbon atoms, preferably from 7 to 9 carbon atoms and any aryl part of the substituent $R^1$ or $R^2$ contains 6 or 10 carbon atoms. Any alkyl, alkenyl or alkynyl group may be linear or branched. A 4- to 6-membered heterocyclic group may be any heterocyclic group with 4 to 6 ring atoms, interrupted by one or more heteroatoms selected from sulfur, nitrogen, and oxygen, preferably oxygen. A halogen atom suitable denotes a fluorine, chlorine or bromine atom.

Likewise, preference is given to compounds of formula I wherein $R^1$ is not hydrogen.

Compounds of formula I are preferred in which $R^1$ represents a straight-chained or branched $C_1$–$C_{10}$ alkyl, in particular a branched $C_3$–$C_{10}$-alkyl group, a $C_3$–$C_8$-cycloalkyl, a $C_5$–$C_9$-bicycloalkyl, a $C_3$–$C_8$-cycloalkyl-$C_1$–$C_6$-alkyl, $C_1$–$C_{10}$-alkoxy-$C_1$–$C_6$-alkyl, a $C_1$–$C_{10}$-haloalkyl or a phenyl group being optionally substituted by one to three halogen atoms or $C_1$–$C_{10}$-alkyl or $C_1$–$C_{10}$-alkoxy groups.

Particular preference is given to compounds I in which $R^2$ represents a hydrogen atom, a $C_1$–$C_{10}$-alkyl or a $C_1$–$C_{10}$-haloalkyl group, in particular a hydrogen atom.

Besides, particular preference is given to compounds I in which $R^2$ is hydrogen.

Moreover, particular preference is given to compounds I in which $R^2$ is methyl.

Furthermore, particular preference is given to compounds I in which $R^2$ is ethyl.

If $R^1$ denotes a $C_1$–$C_{10}$-haloalkyl group, preferably a polyfluorinated alkyl group, in particular a 2,2,2-trifluoroethyl, a 2-(1,1,1-trifluoropropyl) or a 2-(1,1,1-trifluorobutyl) group, $R^2$ preferably represents a hydrogen atom.

If $R^1$ denotes an optionally substituted $C_3$–$C_8$-cycloalkyl group, preferably a cyclopentyl or cyclohexyl group, $R^2$ preferably represents a hydrogen atom or $C_1$–$C_6$-alkyl group.

Moreover, particular preference is given to compounds I in which $R^1$ and $R^2$ together with the interjacent nitrogen atom form an optionally substituted heterocyclic ring, preferably an optionally substituted $C_3$–$C_7$-heterocyclic ring, in particular a pyrrolidine, piperidine, tetrahydropyridine, in particular 1,2,3,6-tetrahydropyridine or azepane ring which is optionally substituted by one or more $C_1$–$C_{10}$-alkyl groups.

Compounds of formula I, in which $R^3$ is 5-fluoro are particularly preferred.

Included in the scope of the present invention are (R) and (S) isomers of compounds of general formula I having a chiral center and the racemates thereof, and salts, N-oxides and acid addition compounds.

Besides, particular preference is given to compounds I in which X represents a chloro atom.

Likewise, particular preference is given to compounds I in which $R^1$ and $R^2$ together with the interjacent nitrogen atom form an optionally substituted 5- or 6-membered ring.

Moreover, particular preference is given to following compounds of formula I:

[5-chloro-6-(5-fluoro-2-trifluoromethyl-phenyl)-7-(4-methyl-piperidin-1-yl)-1,2,4]triazol[1,5-α]pyrimidine,

[5-chloro-6-(5-fluoro-2-trifluoromethyl-phenyl)-[1,2,4]triazolo[1,5-α]pyrimidin-7-yl]-isopropyl-amine,

[5-chloro-6-(5-fluoro-2-trifluoromethyl-phenyl)-[1,2,4]triazolo[1,5-α]pyrimidin-7-yl]-cyclopentyl-amine, bicyclo[2.2.1]hept-2-yl-[5-chloro-6-(5-fluoro-2-trifluoromethylphenyl)-[1,2,4]triazolo(1,5-αpyrimidin-7-yl]-amine, N-[5-chloro-6-(5-fluoro-2-trifluoromethyl-phenyl)-[1,2,4]triazolo[1,5-α]pyrimidin-7-yl]-N,N-diethyl-amine,

[5-chloro-6-(5-fluoro-2-trifluoromethyl-phenyl)-[1,2,4]triazolo[1,5-α]pyrimidin-7-yl]-N-(1-methyl-propyl)-amine,

[5-chloro-6-(5-fluoro-2-trifluoromethyl-phenyl)-1,2,4)triazolo[1,5-α]pyrimidin-7-yl]-(2,2,2-trifluoro-ethyl)-amine,

[5-chloro-6-(5-fluoro-2-trifluoromethyl-phenyl)-[1,2,4]triazolo[1,5-α]pyrimidin-7-yl]-(1,1,1-trifluoro-prop-2-yl)-amine.

With respect to their use, particular preference is given to the compounds I compiled in the tables below. The groups mentioned in the tables for a substituent are furthermore for their part, independently of the combination in which they are mentioned, a particularly preferred embodiment of the respective substituents.

TABLE 1

Compounds of the formula I, in which X is chloro, $(R^3)_n$ is hydrogen and $R^1$ and $R^2$ correspond to one row in Table A

TABLE 2

Compounds of the formula I, in which X is chloro, $(R^3)_n$ is 4-chloro and $R^1$ and $R^2$ correspond to one row in Table A

TABLE 3

Compounds of the formula I, in which X is chloro, $(R^3)_n$ is 5-chloro and $R^1$ and $R^2$ correspond to one row in Table A

TABLE 4

Compounds of the formula I, in which X is chloro, $(R^3)_n$ is 6-chloro and $R^1$ and $R^2$ correspond to one row in Table A

TABLE 5

Compounds of the formula I, in which X is chloro, $(R^3)_n$ is 4-fluoro and $R^1$ and $R^2$ correspond to one row in Table A

TABLE 6

Compounds of the formula I, in which X is chloro, $(R^3)_n$ is 5-fluoro and $R^1$ and $R^2$ correspond to one row in Table A

TABLE 7

Compounds of the formula I, in which X is chloro, $(R^3)_n$ is 6-fluoro and $R^1$ and $R^2$ correspond to one row in Table A

TABLE 8

Compounds of the formula I, in which X is chloro, $(R^3)_n$ is 4-methyl and $R^1$ and $R^2$ correspond to one row in Table A

TABLE 9

Compounds of the formula I, in which X is chloro, $(R^3)_n$ is 5-methyl and $R^1$ and $R^2$ correspond to one row in Table A

TABLE 10

Compounds of the formula I, in which X is chloro, $(R^3)_n$ is 6-methyl and $R^1$ and $R^2$ correspond to one row in Table A

TABLE 11

Compounds of the formula I, in which X is chloro, $(R^3)_n$ is 4-methoxy and $R^1$ and $R^2$ correspond to one row in Table A

TABLE 12

Compounds of the formula I, in which X is chloro, $(R^3)_n$ is 5-methoxy and $R^1$ and $R^2$ correspond to one row in Table A

TABLE 13

Compounds of the formula I, in which X is chloro, $(R^3)_n$ is 6-methoxy and $R^1$ and $R^2$ correspond to one row in Table A

TABLE 14

Compounds of the formula I, in which X is chloro, $(R^3)_n$ is 4-trifluoromethyl and $R^1$ and $R^2$ correspond to one row in Table A

TABLE 15

Compounds of the formula I, in which X is chloro, $(R^3)_n$ is 5-trifluoromethyl and $R^1$ and $R^2$ correspond to one row in Table A

TABLE 16

Compounds of the formula I, in which X is chloro, $(R^3)_n$ is 6-trifluoromethyl and $R^1$ and $R^2$ correspond to one row in Table A

TABLE 17

Compounds of the formula I, in which X is bromo, $(R^3)_n$ is and $R^1$ and $R^2$ correspond to one row in Table A

TABLE 18

Compounds of the formula I, in which X is bromo, $(R^3)_n$ is 4-chloro and $R^1$ and $R^2$ correspond to one row in Table A

TABLE 19

Compounds of the formula I, in which X is bromo, $(R^3)_n$ 5-chloro and $R^1$ and $R^2$ correspond to one row in Table A

TABLE 20

Compounds of the formula I, in which X is bromo, $(R^3)_n$ is 6-chloro and $R^1$ and $R^2$ correspond to one row in Table A

TABLE 21

Compounds of the formula I, in which X is bromo, $(R^3)_n$ is 4-fluoro and $R^1$ and $R^2$ correspond to one row in Table A

TABLE 22

Compounds of the formula I, in which X is bromo, $(R^3)_n$ is 5-fluoro and $R^1$ and $R^2$ correspond to one row in Table A

TABLE 23

Compounds of the formula I, in which X is bromo, $(R^3)_n$ is 6-fluoro and $R^1$ and $R^2$ correspond to one row in Table A

TABLE 24

Compounds of the formula I, in which X is bromo, $(R^3)_n$ is 4-methyl and $R^1$ and $R^2$ correspond to one row in Table A

TABLE 25

Compounds of the formula I, in which X is bromo, $(R^3)_n$ is 5-methyl and $R^1$ and $R^2$ correspond to one row in Table A

TABLE 26

Compounds of the formula I, in which X is bromo, $(R^3)_n$ is 6-methyl and $R^1$ and $R^2$ correspond to one row in Table A

TABLE 27

Compounds of the formula I, in which X is bromo, $(R^3)_n$ is 4-methoxy and $R^1$ and $R^2$ correspond to one row in Table A

TABLE 28

Compounds of the formula I, in which X is bromo, $(R^3)_n$ is 5-methoxy and $R^1$ and $R^2$ correspond to one row in Table A

TABLE 29

Compounds of the formula I, in which X is bromo, $(R^3)_n$ is 6-methoxy and $R^1$ and $R^2$ correspond to one row in Table A

TABLE 30

Compounds of the formula I, in which X is bromo, $(R^3)_n$ is 4-trifluoromethyl and $R^1$ and $R^2$ correspond to one row in Table A

TABLE 31

Compounds of the formula I, in which X is bromo, $(R^3)_n$ is 5-trifluoromethyl and $R^1$ and $R^2$ correspond to one row in Table A

TABLE 32

Compounds of the formula I, in which X is bromo, $(R^3)_n$ is 6-trifluoromethyl and $R^1$ and $R^2$ correspond to one row in Table A

TABLE A

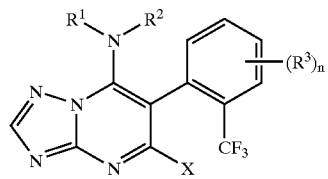

I

| No. | $R^1$ | $R^2$ |
|---|---|---|
| A-1 | $CH_2CH_3$ | H |
| A-2 | $CH_2CH_3$ | $CH_3$ |
| A-3 | $CH_2CH_3$ | $CH_2CH_3$ |
| A-4 | $CH_2CF_3$ | H |

TABLE A-continued $$\text{Structure I with } R^1R^2N\text{- group, triazolopyrimidine core, phenyl with }(R^3)_n\text{ and }CF_3, \text{ and X}$$

| No. | R¹ | R² |
|---|---|---|
| A-5 | CH₂CF₃ | CH₃ |
| A-6 | CH₂CF₃ | CH₂CH₃ |
| A-7 | CH₂CCl₃ | H |
| A-8 | CH₂CCl₃ | CH₃ |
| A-9 | CH₂CCl₃ | CH₂CH₃ |
| A-10 | CH₂CH₂CH₃ | H |
| A-11 | CH₂CH₂CH₃ | CH₃ |
| A-12 | CH₂CH₂CH₃ | CH₂CH₃ |
| A-13 | CH(CH₃)₂ | H |
| A-14 | CH(CH₃)₂ | CH₃ |
| A-15 | CH(CH₃)₂ | CH₂CH₃ |
| A-16 | (±) CH(CH₃)—CH₂CH₃ | H |
| A-17 | (±) CH(CH₃)—CH₂CH₃ | CH₃ |
| A-18 | (±) CH(CH₃)—CH₂CH₃ | CH₂CH₃ |
| A-19 | (R) CH(CH₃)—CH₂CH₃ | H |
| A-20 | (R) CH(CH₃)—CH₂CH₃ | CH₃ |
| A-21 | (R) CH(CH₃)—CH₂CH₃ | CH₂CH₃ |
| A-22 | (S) CH(CH₃)—CH₂CH₃ | H |
| A-23 | (S) CH(CH₃)—CH₂CH₃ | CH₃ |
| A-24 | (S) CH(CH₃)—CH₂CH₃ | CH₂CH₃ |
| A-25 | (±) CH(CH₃)—CH(CH₃)₂ | H |
| A-26 | (±) CH(CH₃)—CH(CH₃)₂ | CH₃ |
| A-27 | (±) CH(CH₃)—CH(CH₃)₂ | CH₂CH₃ |
| A-28 | (R) CH(CH₃)—CH(CH₃)₂ | H |
| A-29 | (R) CH(CH₃)—CH(CH₃)₂ | CH₃ |
| A-30 | (R) CH(CH₃)—CH(CH₃)₂ | CH₂CH₃ |
| A-31 | (S) CH(CH₃)—CH(CH₃)₂ | H |
| A-32 | (S) CH(CH₃)—CH(CH₃)₂ | CH₃ |
| A-33 | (S) CH(CH₃)—CH(CH₃)₂ | CH₂CH₃ |
| A-34 | (±) CH(CH₃)—C(CH₃)₃ | H |
| A-35 | (±) CH(CH₃)—C(CH₃)₃ | CH₃ |
| A-36 | (±) CH(CH₃)—C(CH₃)₃ | CH₂CH₃ |
| A-37 | (R) CH(CH₃)—C(CH₃)₃ | H |
| A-38 | (R) CH(CH₃)—C(CH₃)₃ | CH₃ |
| A-39 | (R) CH(CH₃)—C(CH₃)₃ | CH₂CH₃ |
| A-40 | (S) CH(CH₃)—C(CH₃)₃ | H |
| A-41 | (S) CH(CH₃)—C(CH₃)₃ | CH₃ |
| A-42 | (S) CH(CH₃)—C(CH₃)₃ | CH₂CH₃ |
| A-43 | (±) CH(CH₃)—CF₃ | H |
| A-44 | (±) CH(CH₃)—CF₃ | CH₃ |
| A-45 | (±) CH(CH₃)—CF₃ | CH₂CH₃ |
| A-46 | (R) CH(CH₃)—CF₃ | H |
| A-47 | (R) CH(CH₃)—CF₃ | CH₃ |
| A-48 | (R) CH(CH₃)—CF₃ | CH₂CH₃ |
| A-49 | (S) CH(CH₃)—CF₃ | H |
| A-50 | (S) CH(CH₃)—CF₃ | CH₃ |
| A-51 | (S) CH(CH₃)—CF₃ | CH₂CH₃ |
| A-52 | (±) CH(CH₃)—CCl₃ | H |
| A-53 | (±) CH(CH₃)—CCl₃ | CH₃ |
| A-54 | (±) CH(CH₃)—CCl₃ | CH₂CH₃ |
| A-55 | (R) CH(CH₃)—CCl₃ | H |
| A-56 | (R) CH(CH₃)—CCl₃ | CH₃ |
| A-57 | (R) CH(CH₃)—CCl₃ | CH₂CH₃ |
| A-58 | (S) CH(CH₃)—CCl₃ | H |
| A-59 | (S) CH(CH₃)—CCl₃ | CH₃ |
| A-60 | (S) CH(CH₃)—CCl₃ | CH₂CH₃ |
| A-61 | CH₂C(CH₃)=CH₂ | H |
| A-62 | CH₂C(CH₃)=CH₂ | CH₃ |
| A-63 | CH₂C(CH₃)=CH₂ | CH₂CH₃ |
| A-64 | cyclopentyl | H |
| A-65 | cyclopentyl | CH₃ |
| A-66 | cyclopentyl | CH₂CH₃ |
| A-67 | —(CH₂)₂CH(CH₃)(CH₂)₂— | |

Due to excellent activity, the compounds of formula I may be used in cultivation of all plants where infection by phytopathogenic fungi is not desired, e.g. cereals, solanaceous crops, vegetables, legumes, apples, vine.

The compounds of formula I are superior through their valuable fungicidal properties, in particular their enhanced systemicity and enhanced fungicitoxity.

Moreover, the compounds I are suitable for controlling harmful fungi such as Paecilomyces variotii in the protection of materials (e.g. wood, paper, paint dispersions, fibers and tissues) and in the protection of stored products.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

For example, they can be used in agriculture or related fields for the control of phytopathogenic fungi such as *Alternaria solani, Botrytis cinerea, Cercospora arachidicola, Cochliobolus miiyabeanus, Cercospora beticola, Cladosporium herbarum, Corticium rolfsii, Erysiphe graminis, Erysiphe cichoracearum* und *Sphaerotheca fuliginea, Fusarium-species, Helminthosporium tritici repentis, Leptosphaeria nodorum, Micronectriella nivalis, Monilinia fructigena, Mycosphaerella ligulicola, Mycosphaerella pinodes, Phytophthora infestans, Plasmopara viticola, Pseudocercosporella herpotrichoides*, Puccinia-species, *Pyricularia oryzae, Rhizootonia solani, Sclerotinia sclerotiorum, Uncinula necator* and *Venturia inequalis*. The compounds of formula I according to the Invention possess a high fungicidal activity within a wide concentration range.

The new compounds show an excellent fungicidal activity in various crops.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

The compounds of general formula I have been found to have fungicidal activity. Accordingly, the invention further provides a fungicidal composition which comprises an active ingredient, which is at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may for example be a plant, seed, soil, or water in which a plant grows, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels, tablets and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or γ-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral filters, such as calcite, talc, kaolin, montmorillonite or attapulgite. The physical properties may be improved by addition of highly dispersed silica gel or polymers.

Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, tablets, solutions, emulsifiable concentrates, emulsions, suspension concentrates and aerosols.

Wettable powders usually contain 5 to 90% w/w of active ingredient and usually contain in addition to solid inert carrier, 3 to 10% w/w of dispersing and wetting agents and, where necessary, 0 to 10% w/w of stabilizer(s) and/or other additives such as penetrants or stickers.

Dusts are usually formulated as a dust concentrate having a similar compositions to that of a wettable powder but without a dispersant, and may be diluted in the field with further solid carrier to give a composition usually containing 0.5 to 10% w/w of active ingredient.

Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents.

The so-called "dry flowables" consist of relatively small granules having a relatively high concentration of active ingredient. Emulsifiable concentrates usually contain, in addition to a solvent or a mixture of solvents, 1 to 80 % w/v active ingredient, 2 to 20% w/v emulsifiers and 0 to 20% w/v of other additives such as stabilizers, penetrants and corrosion inhibitors.

Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10 % w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the acitve ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

Emulsion Concentrate (EC)

| | | |
|---|---|---|
| Active Ingredient | Compound of Table I | 30% (w/v) |
| Emulsifier(s) | Atlox ® 4856/Atlox ® 4858 B[1] (mixture containing calcium alkyl aryl sulfonate, fatty alcohol ethoxylates and light aromatics/ mixture containing calcium alkyl aryl sulfonate, fatty alcohol ethoxylates and light aromatics) | 5% (w/v) |
| Solvent | Shellsol ® A[2] (mixture of $C_9$–$C_{10}$ aromatic hydrocarbons) | to 1000 ml |

Suspension Concentrate (SC)

| | | |
|---|---|---|
| Active Ingredient | Compound of Table I | 50% (w/v) |
| Dispersing agent | soprophor ® FL[3] (polyoxyethylene polyaryl phenyl ether phosphate amine salt) | 3% (w/v) |
| Antifoaming agent | Rhodorsil ® 422[3] (nonionic aqueous emulsion of polydimethylsiloxanes) | 0.2% (w/v) |
| Structure agent | Kelzan ® S[4] (Xanthan gum) | 0.2% (w/v) |
| Antifreezing agent | Propylene glycol | 5% (w/v) |
| Biocidal agent | Proxel ®[5] (aqueous dipropylene glycol solution containing 20% 1,2-benisothiazolin-3-one) | 0.1% (w/v) |
| Water | | to 1000 ml |

Wettable Powder (WP)

| | | |
|---|---|---|
| Active Ingredient | Compound of Table I | 60% (w/w) |
| Wetting agent | Atlox ® 4995[1] (polyoxyethylene alkyl ether) | 2% (w/w) |
| Dispersing agent | Witcosperse ® D-60[6] (mixture of sodium salts of condensed naphthalene sulfonic acid and alkylarylpolyoxy acetates | 3% (w/w) |
| Carrier/Filler | Kaolin | 35% (w/w) |

Water Dispersible Granules (WG)

| | | |
|---|---|---|
| Active Ingredient | Compound of Table I | 50% (w/w) |
| Dispersing/Binding agent | Witcosperse ® D-450[6] (mixture of sodium salts of condensed naphthalene sulfonic acid and alkyl sulfonates) | 8% (w/w) |
| Wetting agent | Morwet ® EFW[6] (formaldehyde condensation product) | 2% (w/w) |
| Antifoaming agent | Rhodorsil ® EP 6703[3] (encapsulated silicone) | 1% (w/w) |
| Disintegrant | Agrimer ® ATF[7] (crosslinked homopolymer of N-vinyl-2-pyrrolidone) | 2% (w/w) |
| Carrier/Filler | Kaolin | 35% (w/w) |

1) commercially available from ICI Surfactants
2) commercially available from Deutsche Shell AG
3) commercially available from Rhône-Poulenc
4) commercially available from Kelco Co.
5) commercially available from Zeneca
6) commercially available from Witco
7) commercially available from International Speciality Products The compositions of this invention can be applied to the plants or their environment simultaneous with or in succession with other active substances. These other active substances can be either fertilisers, agents which donate trace elements or other preparations which influence plant growth. However, they can also be selective herbicides, insecticides, fungicides, bactericides, nematicides, algicides, molluscicides, rodenticides, virucides, compounds inducing resistance into plants, biological control agents such as viruses, bacteria, nematodes, fungi and other microorganisms, repellents of birds and animals, and plant growth regulators, or mixtures of several of these preparations, if appropriate together with other carrier substances conventionally used in the art of formulation, surfactants or other additives which promote application.

Furthermore, the other pesticide can have a synergistic effect on the pesticidal activity of the compound of general formula I.

The other fungicidal compound can be, for example, one which is also capable of combating diseases of cereals (e.g. wheat) such as those caused by Erysipha, Puccinia, Septoria, Gibberella and Helminthosporium spp., seed and soil borne diseases and downy and powdery mildews on vines, early and late blight on solanaceous crops, and powdery mildew and scab on apples etc. These mixtures of fungicides can have a broader spectrum of activity than the compound of general formula I alone. Furthermore, the other fungicide can have a synergistic effect on the fungicidal activities of the compound of general formula I.

Examples of the other fungicidal compounds are anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenamidone, fenarimol, fenbuconazole, fenfuram, fenhexamid, fenoxanil, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, IKF-916, imazalil, iminoctadine, ipconazole, iprodione, isoprothiolane, iprovalicarb, kasugamycin, KH-7281, kitazin P, kresoximmethyl, mancozeb, maneb, mepanipyrim, mepronil, metalaxyl, metoonazole, methfuroxam, MON 65500, myclobutanil, neoasozin, nickel dimethyldithiocarbamate, nitrothalisopropyl, nuarimol, ofurace, organo mercury compounds, oxadixyl, oxycarboxin, penconazole, pencycuron, phenazineoxide, phthalide, picoxystrobin, polyoxin D, polyram, probenazole, prochloraz, procymidone, propamocarb, propiconazole, propineb, pyraclostrobin, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, tolclofosmethyl, tolylfluanidt triadimefon, triadimenol, triazbutil, triazoxide, tricyclazole, tridemorph, trifloxystrobin, triflumizole, triforine, triticonazole, validamycin A, vinclozolin, XRD-563, zarilamid, zineb, ziram.

In addition, the co-formulations according to the invention may contain at least one compound of formula I and any of the following classes of biological control agents such as viruses, bacteria, nematodes, fungi, and other microorganisms which are suitable to control insects, weeds or plant diseases or to induce host resistance in the plants. Examples of such biological control agents are: *Bacillus thuringiensis, Verticillium lecanii, Autographica californica* NPv, *Beauvario bassiana, Ampelomyces quisqualis, Bacilis subtilis,*

*Pseudomonas chlororaphis, Pseudomonas fluorescens, Steptomyces griseoviridis* and *Trichoderma harzianum*.

Moreover, the co-formulations according to the invention may contain at least one compound of formula I and a chemical agent that induces the systemic acquired resistance in plants such as for example isonicotinic acid or derivatives thereof, 2,2-dichloro-3,3-dimethylcyclopropylcarboxylic acid or BION.

The compounds of general formula I can be mixed with soil, peat or other rooting media for the protection of the plants against seed-borne, soil-borne or foliar fungal diseases.

The invention still further provides the use as a fungicide of a compound of the general formula I as defined above or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop and ornamental plants against fungal attack. Typical crops which may be protected include vines, grain crops such as wheat and barley, rice, sugar beet, top fruit, peanuts, potatoes, vegetables and tomatoes. The duration of the protection is normally dependent on the individual compound selected, and also a variety of external factors, such as climate, whose impact is normally mitigated by the use of a suitable formulation.

SYNTHESIS EXAMPLES

With due modification of the starting compounds, the protocols shown in the synthesis examples below were used for obtaining further compounds I. The resulting compounds, together with physical data, are listed in the Table which follows.

Example 1

Preparation of Ethyl 2-(5-Fluoro-2-trifluormethyl-phenyl)-acetate

A mixture of 2-(5-fluoro-2-trifluoromethyl-phenyl)-acetic acid (50 g), ethanol (100 ml) and concentrated sulfuric acid (4 ml) is heated at reflux for twelve hours. The solvent is distilled off in vacuo and the residue is diluted with ether. The mixture is neutralized with solid sodium bicarbonate and dried with anhydrous sodium sulphate and filtered. The filtrate is concentrated in vaouo to yield 54 g of the product.

Example 2

Preparation of Diethyl (5-Fluoro-2-trifluoromethyl-phenyl)-malonate

Ethyl 2-(5-fluoro-2-trifluormethyl-phenyl)-acetate (54 g), obtained in Example 1) is slowly added to a mixture of diethylcarbonate (250 ml) and sodium ethoxide (15 g) which is heated at reflux. The solvent is distilled off and the residue is diluted with ethyl acetate. The mixture is acidified with dilute hydrochloric acid. The organic layer is separated and dried with anhydrous sodium sulphate and filtered. The filtrate is concentrated in vacuo to yield 56 g of the product.

Example 3

Preparation of 5,7-Dihydroxy-6-(5-fluoro-2-trifluoro-methyl-phenyl)-[1,2,4]-triazolo[1.5α]pyrimidine A mixture of 3-amino-1,2,4-triazole (14 g), diethyl (5-fluoro-2-trifluoromethyl-phenyl)-malonate (0.17 mol, obtained from Example 2) and tributylamine (50 ml) is heated at reflux at 180° C. for six hours. The reaction mixture is cooled to 70° C. Aqueous sodium hydroxide (21 g/200ml H₂O) is added and the reaction mixture is stirred for 30 minutes. The organic phase is separated off and the aqueous phase is extracted with diethylether. The aqueous phase is acidified with concentrated hydrochloric acid. A brown precipitate is collected by filtration and dried to yield 30 g of the product, mp. 120° C.

Example 4

Preparation of 5,7-Dichloro-6-(5-fluoro-2-trifluoro-methyl-phenyl)-[1,2,4]-triazolo[1.5α]pyrimidine A mixture of 5,7-dihydroxy-6-(5-fluoro-2-trifluoromethyl-phenyl)-[1,2,4]-triazolo[1,5-α]pyrimidine (30 g, obtained from Example 3) and phosphorous oxychloride (50 ml) is heated at reflux at 120° C. for eight hours. Phosphorous oxychloride is partly distilled of. The residue is poured into a mixture of dichloromethane and water. The organic layer is separated, dried with anhydrous sodium sulphate and filtered. The filtrate is concentrated in vacuo and then applied onto a flash chromatography column. The column is consecutively eluted with ethyl acetate/petrol ether (3:7 v/v) to yield 6.1 g of the product, mp. 152° C.

Example 5

Preparation of 5-Chloro-6-(5-fluoro-2-trifluorome-thylphenyl)-7-(4-methyl-piperidin-1-yl)-[1,2,4] triazolo[1,5-α]pyrimidine.

A mixture of 4-methylpiperidine(1.42 mmoles), triethylamine (1.42 mmoles) and dichloromethane (10 ml) is added to a mixture of 5,7-dichloro-6-(5-fluoro-2-trifluoromethyl-phenyl)-[1,2,4]-triazolo[1,5-α]pyrimidine (1.42 mmol) and dichloromethane (30 ml) under stirring. The reaction mixture is stirred 48 hours at room temperature and subsequently washed with dilute hydrochloric acid (5%). The organic layer is separated, dried with anhydrous sodium sulfate and filtered. The filtrate is evaporated under reduced pressure to yield 0.34 g of white crystals having a melting point of 149° C.

TABLE I

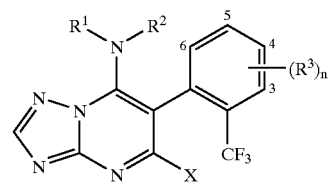

I

| No. | R¹ | R² | (R³)ₙ | X | phys. data (m.p. [° C.]) |
|---|---|---|---|---|---|
| I-1 | CH(CH₃)₂ | H | 5-F | Cl | 63 |
| I-2 | cyclopentyl | H | 5-F | Cl | 118 |
| I-3 | norborn-2-yl | H | 5-F | Cl | 160 |
| I-4 | CH₂CH₃ | CH₂CH₃ | 5-F | Cl | 132 |
| I-5 | 2-butyl | H | 5-F | Cl | 124 |
| I-6 | CH₂CF₃ | H | 5-F | Cl | 118 |
| I-7 | H | H | 5-F | Cl | 243 (decomp.) |
| I-8 | cyclopentyl | H | H | Br | 190 |
| I-9 | norborn-2-yl | H | H | Br | 187 |
| I-10 | CH₂CH₃ | CH₂CH₃ | H | Br | 131 |
| I-11 | CH(CH₃)₂ | H | H | Br | 134 |

TABLE I-continued

I $$R^1\text{-}N\text{-}R^2 \text{ [triazolopyrimidine with phenyl-CF}_3\text{ ring (R}^3\text{)}_n\text{, and X]}$$

| No. | $R^1$ | $R^2$ | $(R^3)_n$ | X | phys. data (m.p. [° C.]) |
|---|---|---|---|---|---|
| I-12 | $CH_3$ | H | H | Br | 196 |
| I-13 | $CH_2CH_3$ | H | H | Br | 193 |
| I-14 | —$(CH_2)_6$— | | H | Cl | 148 |
| I-15 | —$(CH_2)_5$— | | H | Cl | 164 |
| I-16 | —$(CH_2)_2CH(CH_3)(CH_2)_2$— | | H | Cl | 177 |
| I-17 | cyclopentyl | H | 4-F | Cl | 213 |
| I-18 | $CH(CH_3)_2$ | H | 4-F | Cl | 161 |
| I-19 | $CH_2C(CH_3)=CH_2$ | $CH_2CH_3$ | 4-F | Cl | 119 |
| I-20 | $CH_2CH_3$ | $CH_2CH_3$ | 4-F | Cl | 141 |
| I-21 | cyclopropyl | H | 4-F | Cl | 155 |
| I-22 | —$(CH_2)_6$— | | 4-F | Cl | 193 |
| I-23 | cycloheptyl | H | H | Cl | 191 |
| I-24 | $CH_2CH(CH_3)_2$ | H | H | Cl | 164 |
| I-25 | —$CH_2CH(CH_3)(CH_2)_3$— | | H | Cl | 178 |
| I-26 | —$(CH_2)_2CH(OH)(CH_2)_2$— | | H | Cl | 187 |
| I-27 | —$(CH_2)_2CH(CF_3)(CH_2)_2$— | | H | Cl | 245 |
| I-28 | $CH(CH_3)CH_2CH_3$ | H | H | Cl | 128 |
| I-29 | —$(CH_2)_2CHCl(CH_2)_2$— | | H | Cl | 185 |
| I-30 | —$(CH_2)_2CH(CH_3)(CH_2)_2$— | | 6-F | Cl | 131 |
| I-31 | cyclopentyl | H | 6-F | Cl | 131 |
| I-32 | $CH_2C(CH_3)=CH_2$ | $CH_2CH_3$ | 6-F | Cl | 123 |
| I-33 | $CH(CF_3)CH_3$ | H | 4-F | Cl | 217 |
| I-34 | $CH(CF_3)CH_3$ | H | 4-$OCH_3$ | Cl | 165 |

Biological Investigations

A Determination of Minimum Inhibitory Concentration by Test Compounds in the Serial Dilution Test The MIC (Minimum Inhibitory Concentration) value, which indicates the lowest concentration of the active ingredient in the growth medium which causes a total inhibition of myecelial growth, is determined by serial dilution test using Microtiter plates with 24 or 48 wells per plate. The dilution of the test compounds in the nutrient solution and the distribution to the wells is carried out by a TECAN RSP 5000 Robotic Sample Processor. The following test compound concentrations are used: 0.04, 0.10, 0.20, 0.39, 0.78, 1.56, 3.13, 6.25, 12.50, 25.00, 50.00 and 100.00 µg/ml (alternatively a starting concentration of 5.00 ppm with 12 serial dilutions were used). For preparation of the nutrient solution, V8 vegetable juice (333 ml) is mixed with calcium carbonate (4.95 g), centrifuged, the supernatant (200 ml) diluted with water (800 ml) and autoclaved at 121° C. for 30 min.

The respective inocula (*Alternaria solani*, ALTESO; *Botrytis cinerea*, BOTRCI; *Cochliobulus sativus*, COCHSA; *Magnaporthe grisea* f. sp. Oryzae, PYRIOR; are added into the wells as spore suspensions (50 ml; $5\times10^5$/ml) or agar slices (6 mm) of an agar culture of the fungus.

After 6–12 days incubation at suitable temperatures (18–25° C.), the MIC values are determined by visual of the plates (Table II).

TABLE II

| Compound | ALTEBO | BOTRCI | COCHSA | PYRIOR |
|---|---|---|---|---|
| Example 5 | 0.2 | 0,78 | 0.78 | <0.05 |
| I-1 | 100 | 50 | 25 | 1.56 |
| I-2 | 3.13 | 25 | 3.13 | 0.78 |
| I-3 | 0.78 | 25 | 6.25 | 12.5 |
| I-4 | >100 | 25 | 12.5 | 0.78 |
| I-5 | 6.25 | 12.5 | 12.5 | 0.78 |

B Evaluation of in Vivo Fungicidal Activity of Test Compounds

Test compounds are dissolved in acetone and diluted with deionized water (95 parts water to 5 parts acetone) containing 0.05% TWEEN 20®, a polyoxyethylene sorbitan monolaurate surfacant manufactured by Atlas Chemical Industries, to give a concentration of 200 ppm.

The plants are sprayed with the test solutions, dried and inoculated with fungi later the same day when disease symptom development is optimal, the plants are rated for disease control. Each test contains inoculated treated plants, inoculated untreated plants an inoculated plants treated with reference fungicides. The data obtained are the following:.

Use Example 1

Action on *Rhizoctonia solani*

In this test compounds Example 5, I-1, I-2, I-4, I-5, I-6, I-28 and I-30 to I-34 showed at least 90% control.

Use Example 2

Action on *Cercospora beticola*

In this test compounds Example 5, I-1 to I-6, I-8 to, I-9, I-17, I-22 and I-28 to I-32 showed more than 95% control.

Use Example 3

Action on *Alternaria solani*

In this test compounds Example 5, I-1 to I-6, I-8, I-9, I-17, I-22 and I-28 to I-34 showed at least 75% control.

C Evaluation of In vitro Fungicidal Activity against *Rhizoctonia solani*

Test compounds are dissolved in acetone to give a concentration of 25 ppm and added to individual cell walls (24-cell-well-plates, Corning), which were previously filled with a suspension of ground fungal mycelium in a chemically defined growth medium. After 3–7 days of incubation, inhibition of mycelial growth is recorded using the following scale: The data obtained are shown in Table IV.

Rating scale

| Rating | Degree of Inhibition |
|---|---|
| 0 | None |
| 3 | slight |
| 5 | moderate |
| 7 | severe |
| 9 | complete |

TABLE IV

| Compound | Rating |
|---|---|
| Example 5 | 7 |
| I-1 | 7 |
| I-2 | 7 |
| I-3 | 5 |
| I-4 | 7 |
| I-5 | 7 |
| I-6 | 7 |
| I-7 | 0 |

What is claimed is:

1. 6-(2-Trifluoromethyl-phenyl)-triazolopyrimidines of formula I

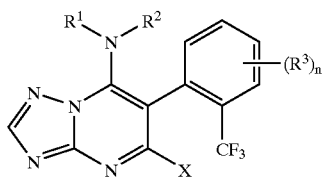

in which
R$^1$ and R$^2$ independently denote hydrogen or
C$_1$–C$_{10}$-alkyl, C$_2$–C$_{10}$-alkenyl, C$_2$–C$_{10}$-alkynyl, C$_4$–C$_{10}$-alkadienyl, or C$_1$–C$_{10}$-haloalkyl, C$_3$–C$_8$-cycloalkyl, C$_5$–C$_{10}$-bicycloalkyl, phenyl, naphthyl, or 5- or 6-membered heterocyclyl, containing one to four nitrogen atoms or one to three nitrogen atoms and one sulfur or oxygen atom, or 5- or 6-membered heteraryl, containing one to four nitrogen atoms or one to three nitrogen atoms and one sulfur or oxygen atom, or where R$^1$ and R$^2$ radicals may be unsubstituted or partially or fully halogenated or may carry one to three groups R$^a$, R$^a$ is halogen, cyano, nitro, hydroxyl, C$_1$–C$_6$-alkyl, C$_1$–C$_6$-haloalkyl, C$_3$–C$_6$-cycloalkyl, C$_1$–C$_6$-alkoxy, C$_1$–C$_6$-haloalkoxy, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_2$–C$_6$-alkynyl, C$_3$–C$_6$-alkynyloxy, and C$_1$–C$_4$-alkylenedioxy, which may be halogenated; or R$^1$ and R$^2$ together with the interjacent nitrogen atom represent a 5- or 6-membered heterocyclic ring, containing one to four nitrogen atoms or one to three nitrogen atoms and one sulfur or oxygen atom, which may be substituted, by one to three R$^a$ radicals;

R$^3$ is hydrogen, halogen, C$_1$–C$_{10}$-alkyl, C$_1$–C$_{10}$-alkoxy and C$_1$–C$_{10}$-haloalkyl;

n is 0 or 1; and

X is halogen.

2. Compounds of formula I according to claim 1 in which (R$^3$)$_n$ is 5-fluoro.

3. Compounds of formula I according to claim 1, in which
R$^1$ is straight chained or branched C$_1$–C$_{10}$-alkyl, C$_1$–C$_{10}$-haloalkyl, straight chained or branched C$_2$–C$_6$-alkenyl, C$_3$–C$_6$-cycloalkyl, C$_5$–C$_8$-bicycloalkyl, and R$^2$ is hydrogen or C$_1$–C$_6$-alkyl, or R$^1$ and R$^2$ together with the interjacent nitrogen atoms represent a heterocyclic ring with 5 or 6 carbon atoms being optionally substituted with one or two C$_1$–C$_6$-alkyl groups.

4. Compounds according to claim 1 in which R$^2$ is hydrogen.

5. Compounds according to claim 1 in which X is chlorine.

6. [5-Chloro-6-(5-fluoro-2-trifluoromethyl-phenyl)-7-(4-methylpiperidin-1-yl)-1,2,4]triazolo[1,5-α]pyrimidine,

[5-Chloro-6-(5-fluoro-2-trifluoromethyl-phenyl)-[1,2,4]triazolo[1,5-α]pyrimidin-7-yl]-isopropyl-amine,

[5-Chloro-6-(5fluoro-2-trifluoromethyl-phenyl)-[1,2,4]triazolo[1,5-α]pyrimidin-7-yl]-cyclopentyl-amine, Bicyclo[2.2.1]hept-2-yl-[5-chloro-6-(5-fluoro-2-trifluoromethyl-phenyl)-[1,2,4]triazolo[1,5-α]pyrimidin-7-yl]-amine, N-[5-Chloro-6-(5-fluoro-2-trifluoromethyl-phenyl)-[1,2,4]triazolo [1,5-α]pyrimidin-7-yl]-N,N-diethylamine,

[5-Chloro-6-(5-fluoro-2-trifluoromethyl-phenyl)-[1,2,4]triazolo[1,5-α]pyrimidin-7-yl]-N-(1-methyl-propyl)-amine,

[5-Chloro-6-(5-fluoro-2-trifluoromethyl-phenyl)-[1,2,4]triazolo[1,5-α]pyrimidin-7-yl]-(2,2,2-trifluoro-ethyl)-amine,

[5-Chloro-6-(5-fluoro-2-trifluoromethyl-phenyl)-[1,2,4]triazolo[1,5-α]pyrimidin-7-yl]-(1,1,1-trifluoroprop-2-yl)-amine.

7. A composition suitable for controlling phytopathogenic fungi, comprising a solid or liquid carrier and a compound of the formula I as claimed in claim 1.

8. A method for controlling phytopathogenic fungi, which comprises treating the fungi or the materials, plants, the soil or the seed to be protected against fungal attack with an effective amount of a compound of the formula I as claimed in claim 1.

* * * * *